United States Patent [19]

Scharschmidt et al.

[11] Patent Number: 5,308,833
[45] Date of Patent: May 3, 1994

[54] METHOD FOR TREATING HEPATITIS B CARRIERS WITH MINIMAL DISEASE

[75] Inventors: Bruce F. Scharschmidt; John D. Baxter, both of San Francisco, Calif.

[73] Assignee: SciClone Pharmaceuticals, San Mateo, Calif.

[21] Appl. No.: 833,468

[22] Filed: Feb. 6, 1992

[51] Int. Cl.⁵ .............................. A61K 37/02
[52] U.S. Cl. ................................... 514/12
[58] Field of Search ......................... 514/12

[56] References Cited

U.S. PATENT DOCUMENTS

| | | | |
|---|---|---|---|
| 4,079,127 | 3/1978 | Goldstein et al. | 514/12 |
| 4,148,788 | 4/1979 | Wang | 530/324 |
| 4,264,571 | 4/1981 | Goldstein et al. | 436/540 |
| 4,339,427 | 7/1982 | Goldstein et al. | 436/540 |
| 4,855,407 | 8/1989 | Wang | 530/334 |

OTHER PUBLICATIONS

Lok et al Dig. Dis., vol. 10(1) 1992 Abstract only.
Hollinger et al Viral Hepatitis, 2nd Ed. N.Y. pp. 84–88.
Barnaba et al The J. of Immunol., vol. 143, No. 8 Oct. 15, 1989 pp. 2650–2655.
McIntyre et al Oxford Textbook of Clin. Hepatol. vol. 1 Oxford Univ. Press, 1991 pp. 571–580, 584–590, 599–603.
Lok et al Gastroentenology, vol. 102 (6) (1992) Abstract only.
Mutchnick et al Hepatology (Baltimore) vol. 8, No. 5, (1988) p. 1270 (Abstract).
Hoofnagle, *New Engl. J. Med.* (1990) 323:337–339.
Blumberg, B. S., et al., Eds., *Vaccine* (1990) vol. 8, Supplement entitled: Proceedings of the International Conference on Prospects for Eradication of Hepatitis B Virus, Geneva 23–24, (Feb. 1989).
Popper et al., *Hepatology* (1987) 7(4):764–772.
Peters et al., *Hepatology* (1991) 13(5):977–994.
Low et al., Thymus (1984) 6:27–42.
Mutchnick et al., *Hepatology* (1991) 14:409–415.

Primary Examiner—Michael G. Wityshyn
Assistant Examiner—Choon P. Koh
Attorney, Agent, or Firm—Morrison & Foerster

[57] ABSTRACT

Methods for treating minimal disease hepatitis B infection are disclosed. Minimal disease carriers are given thymosin α-1, or biologically active fragments or analogs thereof In this way, the indications of hepatitis B can be reduced or eliminated.

9 Claims, No Drawings

METHOD FOR TREATING HEPATITIS B CARRIERS WITH MINIMAL DISEASE

DESCRIPTION

1. Technical Field

The instant invention relates to a method for treating hepatitis B infections. More particularly, the present invention pertains to a method of treating minimal disease hepatitis B carriers using thymosin α-1.

2. Background

Hepatitis B is the most prevalent form of hepatitis and is the second most common infectious disease worldwide. The disease is caused by the hepatitis B virus (HBV), a DNA virus. The virus is transmitted through blood transfusions, contaminated needles, sexual contact and vertical transmission (from mother to child). In addition, a large number of people are infected by unknown means. A description of the virus, its modes of transmission and disease, can be found in, e.g., Hoofnagle, J.H., *New Engl. J. Med.* (1990) 323:337–339; *Vaccine* (1990) vol. 8 suppl.; Popper, H. et al., *Hepatology* (1987) 7:764–772; "*Hepatology, a Textbook of Liver Disease*" (1990) Zakim and Boyer eds., W.B. Sauders Co., 2nd ed.; "*Viral Hepatitis*" (1991) Hollinger, F.B. et al., eds., Raven Press, 2nd ed.

Of adults who become infected with the virus, about 5% develop a long-term infection, i.e., become "carriers" of the virus. Of those infected perinatally, which accounts for most of the hepatitis B infections worldwide, the vast majority (possibly 90%) become carriers. Approximately 5% of the world's population are carriers of HBV, and the majority of carriers are contagious, i.e., they can transmit HBV infection to others via sexual contact, blood or blood products or vertically (at birth).

Carriers of the virus can exhibit various forms of disease including chronic and minimal disease hepatitis. About 50% of the carriers show chronic inflammatory changes in the liver and, of these, about 50% have histopathologic changes (termed "chronic active hepatitis") that can lead to fibrosis and ultimately to cirrhosis and progressive liver failure. Carriers without chronic inflammatory changes may also develop chronic active hepatitis. Liver cancer develops in about 10 to 30% of hepatitis B carriers. It has been estimated that approximately 4 million carriers of hepatitis B virus die each year from liver cancer or cirrhosis.

The persistent infection seen in individuals presenting with chronic hepatitis may be due to a defective or physiologically immature immunological response, resulting in an impaired ability to clear the virus. Although the mechanisms responsible for liver damage are poorly understood, it is thought that in most individuals such damage results from attack by the body's immune system on infected liver cells, rather than from liver destruction by HBV. Cytotoxic T cells appear to be responsible for immune-mediated hepatic damage. The balance between suppression of immune system activity against normal tissue and the immunological response mounted against the virus, also appears to be impaired in chronic hepatitis B. A number of specific immune defects have been described in chronic hepatitis, including defective production of α-interferon by HBV-infected hepatocytes and inhibition of cytotoxic T cell responses (reviewed in Peters, M. et al., *Hepatology* (*United States*) (May 1991) 13(5):977–94).

Roughly 40% of hepatitis B carriers manifest the minimal disease state. A minimal disease carrier is a person who has detectable hepatitis B antigens or viral DNA in the serum, and yet is healthy, has normal serum enzyme levels, and no clinically evident signs or symptoms of liver damage. Minimal disease carriers may progress to chronic active hepatitis which can lead to cirrhosis with liver failure, as described above.

It is not presently understood why some hepatitis B carriers have no inflammation and liver damage, while others do. These two states appear to represent two different phases in the viral infection—an active and a more passive phase, respectively. During the minimal disease phase, carriers do not show overt signs of immunological imbalance, as evidenced by lack of easily observable destruction of hepatic tissue. As explained above, minimal disease carriers can convert to chronic hepatitis. The factors contributing to transition from one state to another are not presently known.

There is currently no effective treatment for minimal disease carriers, yet treatment of such carriers, before they manifest a more serious form of the disease or transmit it to others, would be highly desirable. In addition, because the carrier state can be diagnosed by measuring hepatitis B antigens or DNA in the blood, it would not be necessary to conduct liver biopsies to qualify patients for treatment. Although a vaccine to prevent hepatitis B is available, it is not used on a massive basis and does not alleviate the disease in existing carriers. Thus, even if implemented on a massive scale, such a vaccine would not diminish the need for an effective treatment of individuals with hepatitis B viral infection for at least several decades, due to the large number of carriers and the highly contagious nature of the disease.

Thymosin α-1 is a 28 amino acid peptide. This peptide, originally isolated from calf thymus thymosin fraction 5, is one of several polypeptides present in thymosin fraction 5 which participate in the regulation, differentiation and function of thymic dependent lymphocytes (T-cells). The isolation, characterization and use of thymosin α-1 is described in U.S. Pat. No. 4,079,127.

Although the mechanism(s) by which thymosin α-1 mediates its effects is unknown, evidence suggests that it may function through modulation of the immune system. Thymosin α-1 has been shown to trigger maturational events in lymphocytes, augment T-cell function, and promote reconstitution of immune defects (Low, T.L.K. et al., *Thymus* (1984) 6:27–42). Thymosin has also been shown to cause increases in lymphocyte counts and enhance production of γ-interferon in individuals suffering from chronic active hepatitis B (Mutchnick, M.G. et al., *Hepatology* (1991) 14:409–415).

Mutchnick, M.G. et al., *Hepatology* (1991) 14:409–415, also describes the use of thymosin α-1 in the treatment of chronic active hepatitis B, that is, patients with evidence of liver injury on biopsy. Patients administered the peptide cleared hepatitis B virus DNA from serum and tested persistently negative for serum HBV DNA after treatment was terminated. No asymptomatic carriers without histopathological evidence of liver injury were included in this study; yet such individuals likely account for most carriers worldwide.

DISCLOSURE OF THE INVENTION

The present invention provides a method for treating minimal disease hepatitis B infections. In particular, the present invention pertains to a method of treating with thymosin α-1 HBV carriers who are asymptomatic and have no biochemical or histopathologic evidence of liver disease, yet may ultimately develop serious, progressive liver disease or liver cancer or transmit the infection to others.

Accordingly, in one embodiment, the instant invention is directed to a method for treating minimal disease hepatitis B infection comprising administering to a minimal disease hepatitis B carrier a therapeutically effective amount of at least one peptide selected from the group consisting of thymosin α-1, a biologically active fragment of thymosin α-1, and a biologically active analog of thymosin α-1, in a pharmaceutically acceptable vehicle.

In particularly preferred embodiments, the peptide is thymosin α-1 and the composition is administered subcutaneously.

These and other embodiments of the present invention will readily occur to those of ordinary skill in the art in view of the disclosure herein.

DETAILED DESCRIPTION

The practice of the present invention will employ, unless otherwise indicated, conventional techniques of protein chemistry, molecular biology, microbiology and recombinant DNA technology, which are within the skill of the art. Such techniques are explained fully in the literature. See, e.g., Scopes, R.K., *Protein Purification Principles and Practice.* 2nd ed. (Springer-Verlag 1987); *Methods in Enzymology* (S. Colowick and N. Kaplan eds., Academic Press, Inc.); Sambrook, Fritsch & Maniatis, *Molecular Cloning: A Laboratory Manual,* 2nd ed. (Cold Spring Harbor Laboratory Press 1989); *Oligonucleotide Synthesis* (M.J. Gait ed. 1984); and *Handbook of Experimental Immunology,* Vols. I–IV (D.M. weir and C.C. Blackwell eds., 1986, Blackwell Scientific Publications).

All patents, patent applications and publications mentioned herein, whether supra or infra, are hereby incorporated herein by reference in their entirety.

A. DEFINITIONS

In describing the present invention, the following terms will be employed, and are intended to be defined as indicated below.

By "minimal disease hepatitis B" is meant the disease state present in an asymptomatic carrier of hepatitis B, the carrier being identified as having hepatitis B antigens or HBV DNA in the serum, but appearing healthy, with normal serum enzyme levels, and no biochemical or histopathological evidence of liver disease. The minimal disease state is readily understood and identifiable by a skilled practitioner.

"Thymosin α-1", as used herein, refers to the 28-mer described below, with or without the N-acetyl group, as well as biologically active fragments of this sequence and biologically active analogs of the sequence (i.e. deletion, substitution and addition mutants), which are substantially homologous to the peptide sequence shown below.

A peptide that is "substantially homologous" to thymosin α-1 is one in which at least about 30%, preferably at least about 85% to 90%, and most preferably at least about 95%, of the amino acids match over a defined length of the molecule, with the sequence depicted below.

A "biologically active" fragment or analog of thymosin α-1, is a fragment or analog of thymosin α-1 which retains a significant amount of the activity of the native molecule, i.e., which is capable of decreasing serum HBV DNA and/or hepatitis B surface antigen, as described further below.

The term "treatment" as used herein refers to either (i) the prevention of infection or reinfection (prophylaxis), or (ii) the reduction or elimination of indicators of asymptomatic hepatitis B (therapy).

A "therapeutically effective amount" of thymosin α-1 is an amount of the peptide which has the capability of changing the measurable parameters of hepatitis infection. Since the patients included in the asymptomatic category have normal liver enzyme biochemistry, the parameters that will normally be monitored are serum hepatitis B surface antigen (HBsAg) and serum viral DNA (HBV DNA). Response is defined as a significant decrease of either of these parameters. An amount of peptide which has the ability of eliciting a response is considered a "therapeutically effective amount." HBV DNA can be monitored using the spot hybridization assay described in Mutchnick, M.G. et al., *Hepatology* (1991) 14:409–415 and Lieberman, H.M. et al., *Hepatology* (1983) 3:285–291 Alternatively, the presence of HBV DNA in the blood can be measured using standard PCR technology. See, e.g., U.S. Pat. Nos. 4,683,202 and 4,683,195, incorporated herein by reference in their entirety. Serum HBsAg levels can be monitored using standard RIAs, as described in Mutchnick, M.G. et al., *Hepatology* (1991) 14:409–415 or by standard ELISAs.

B. GENERAL METHODS

The present invention relates to the use of thymosin α-1 for the treatment of minimal disease hepatitis B infection. Thymosin α-1 is one of several peptides present in thymosin fraction 5 from the thymus gland. The native molecule is a 28-mer, having the following amino acid sequence:

(SEQ ID NO:1)
Ac—Ser—Asp—Ala—Ala—Val—Asp—Thr—Ser—Ser—Glu—
Ile—Thr—Thr—Lys—Asp—Leu—Lys—Glu—Lys—Lys—Glu—
Val—Val—Glu—Glu—Ala—Glu—Asn—OH.

Thymosin α-1, as well as fragments and analogs thereof, are easily synthesized using standard methods of peptide synthesis, known to those of skill in the art. U.S. Pat. Nos. 4,148,788 and 4,855,407 describe the solution phase and solid phase synthesis, respectively, of thymosin α-1, and are incorporated herein by reference in their entirety. See, also, Young, J.D., *Solid Phase Peptide Synthesis,* 2nd ed. (Pierce Chemical Company 1984); and Barany, G. and Merrifield, R.B., *The Peptides: Analysis, Synthesis, Biology.* Vol. 2 (Gross, E. and Meienhofer, J. eds., Academic Press 1980), for a discussion of solid phase peptide synthesis; and Bodansky, M. *Principles of Peptide Synthesis* (Springer-Verlag 1984); and *The Peptides: Analysis, Synthesis, Biology.* Vol. 1 (Gross, E. and Meienhofer, J. eds., Academic Press 1980), for solution phase peptide synthesis.

Thymosin α-1 can also be isolated directly from appropriate tissue expressing the same, using techniques readily known in the art. This is generally accomplished by first preparing a crude tissue extract which lacks cellular components and several extraneous proteins. The thymosin α-1 can then be further purified i.e. by column chromatography, HPLC, immunoadsorbent techniques or other conventional methods well known in the art. U.S. Pat. No. 4,079,127 discloses a method for purifying thymosin α-1 from calf thymus and is incorporated herein by reference in its entirety.

Finally, thymosin α-1 and fragments or analogs thereof, may be produced recombinantly using methods well known to those of skill in the art. See, e.g. Sambrook, Fritsch & Maniatis, *Molecular Cloning: A Laboratory Manual,* 2nd ed. (Cold Spring Harbor Laboratory Press 1989); *Oligonucleotide Synthesis* (M.J. Gait ed. 1984)

Thymosin α-1, or an active fragment thereof, or an analog thereof, can be administered to subjects diagnosed or suspected of having minimal disease hepatitis B infection. The thymosin α-1 may be administered alone or mixed with a pharmaceutically acceptable vehicle or excipient.

Typically, the thymosin α-1 compositions are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. As explained above, the active ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. *See, e.g.,* Remington's Pharmaceutical Sciences, Mack Publishing Company, Easton, Pa., 15th edition, 1975. The composition or formulation to be administered will, in any event, contain a quantity of the peptide adequate to reduce or eliminate HDV DNA and/or HBsAg from the serum of the subject being treated.

The injectable compositions are typically administered by subcutaneous or intramuscular injection. However, intravenous injection is also acceptable. Injectable formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on such factors as the age, weight and degree of health of the subject to be treated. With the present formulations, between about 600 to 1500 μg, more preferably 900 to 1200 μg, of thymosin α-1 per square meter of body area will be administered. Other effective dosages can be readily established by one of ordinary skill in the art through routine trials establishing dose response curves.

Additional formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the peptide into carriers or vehicles such as liposomes, nonresorbable impermeable polymers such as ethylenevinyl acetate copolymers and Hytrel ® copolymers, swellable polymers such as hydrogels, or resorbable polymers such as collagen and certain polyacids or polyesters such as those used to make resorbable sutures. The peptides can also be presented using implanted mini-pumps, well known in the art.

Furthermore, the peptides may be formulated into compositions in either neutral or salt forms. Pharmaceutically acceptable salts include the acid addition salts (formed with the free amino groups of the active peptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The subject is treated by administration of the thymosin α-1 peptide, or fragment thereof, or analog thereof, in at least one dose. Preferably, thymosin α-1 is administered from one to several times weekly for several weeks to several months. More preferably, the compositions are given one to four times weekly, most preferably twice weekly, for at least about three to about twelve months, most preferably for at least about six months. The progress of treatment can be monitored by measuring the presence of HBV DNA and/or HBsAg, as described above.

Below are examples of specific embodiments for carrying out the present invention. The examples are offered for illustrative purposes only, and are not intended to limit the scope of the present invention in any way.

EXAMPLE 1

A randomized, open trial with a total sample size of 40 patients is conducted. Patients included in the study are at least 18 years of age and are hepatitis B surface antigen ("HBsAg") seropositive for at least 6 months. The patients also have HBV DNA in their serum for at least 3 months (as measured by PCR or any other standard detection method). Only patients with minimal disease are included; these patients would have normal plasma levels of hepatic enzymes and, if performed, minimal or no inflammatory changes on liver biopsy, including no evidence for scarring or cirrhosis.

Subjects which have had previous therapy with interferon within 1 year, HIV infection with HIV seropositivity confirmed by Western blot, or the presence of hepatitis C virus (HCV) antibody, are excluded from the study, as well as pregnant subjects or subjects who have engaged in intravenous drug abuse within the previous 5 years.

Patients undergo a pretreatment exam monthly for at least 3 months prior to the treatment protocol. Examination includes:

1. Blood studies including FBC with differentiated count, prothrombin time (PT), glucose, creatinine and electrolytes, liver function tests (LFT), α-fetoprotein (AFP), HIV antibody, HCV antibody, hepatitis-Δ antibody, HB markers (HBsAg and HBV DNA) and thymosin α-1 levels.

2. Liver biopsy and liver HBV DNA analysis.

3. Routine urinalysis.

4. Women of child bearing age will have a pregnancy test.

Selected patients are randomized into two groups (group 1 patients will receive thymosin α-1 treatment, and group 2 patients a placebo). Group 1 patients are given thymosin α-1 at a dosage of 1600 μg/injection by the subcutaneous route twice weekly for 6 months. Group 2 patients receive placebo injections under the same regimen. All patients are seen at 2 and 4 weeks from the start of the treatment, and thereafter at monthly intervals during the 6 month treatment period. They are also monitored monthly for 6 months to two years after completion of treatment.

Response to treatment is defined by loss of serum HBV DNA or serum HBsAg. A responder is a patient with decreased levels of serum HBV DNA or HBsAg achieved and sustained during the 12 month study. A nonresponder has no changes in either serum HBV DNA or HBsAg at the conclusion of the study (12 months). Relapse status is given to patients who initially lose HBV DNA in their serum but regain the DNA by the conclusion of the study.

Group means are compared by Student's two-tailed t test. Changes in measurement between the inclusion values and subsequent time points are compared by Student's two-tailed paired t test or the Wilcoxon paired sample test.

Patients are monitored for any significant side effects or allergic manifestations resulting from the treatment.

Thus, methods of treating minimal disease hepatitis B infection are disclosed. Although preferred embodiments of the subject invention have been described in some detail, it is understood that obvious variations can be made without departing from the spirit and scope of the invention as defined by the appended claims.

---

We claim:

1. A method for treating minimal disease hepatitis B infection comprising administering to a minimal disease hepatitis B carrier a therapeutically effective amount of at least one peptide selected from the group consisting of thymosin α-1, a biologically active fragment of thymosin α-1 and a biologically active analog of thymosin α-1, in a pharmaceutically acceptable vehicle.

2. The method of claim 1 wherein said peptide is thymosin α-1.

3. The method of claim 1 wherein said peptide is a biologically active fragment of thymosin α-1.

4. The method of claim 1 wherein said peptide is a biologically active analog of thymosin α-1.

5. The method of claim 1 wherein said administering is done subcutaneously.

6. The method of claim 1 wherein from about 600 to about 1500 μg of said peptide per square meter of body area is administered.

7. The method of claim 1 wherein from about 900 to about 1200 μg of said peptide per square meter of body area is administered.

8. The method of claim 6 wherein said peptide is administered twice weekly.

9. The method of claim 7 wherein said peptide is administered twice weekly.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
    (A) LENGTH: 28 amino acids
    (B) TYPE: amino acid
    (C) STRANDEDNESS: single
    (D) TOPOLOGY: linear (xi) SEQUENCE DESCRIPTION: SEQ ID NO:1:

```
Ser Asp Ala Ala Val Asp Thr Ser Ser Glu Ile Thr Thr Lys Asp Leu
 1               5                  10                      15

Lys Glu Lys Lys Glu Val Val Glu Glu Ala Glu Asn
                20                  25
```